United States Patent
Konstantino et al.

(10) Patent No.: US 7,686,824 B2
(45) Date of Patent: Mar. 30, 2010

(54) APPARATUS AND METHODS FOR TREATING HARDENED VASCULAR LESIONS

(75) Inventors: Eitan Konstantino, Orinda, CA (US); Tanhum Feld, Moshav Merhavya (IL); Nimrod Tzori, Sunnyvale, CA (US)

(73) Assignee: AngioScore, Inc., Fremont, CA (US)

( * ) Notice: Subject to any disclaimer, the term of this patent is extended or adjusted under 35 U.S.C. 154(b) by 1091 days.

(21) Appl. No.: 10/631,499

(22) Filed: Jul. 30, 2003

(65) Prior Publication Data
US 2004/0143287 A1   Jul. 22, 2004

Related U.S. Application Data

(60) Provisional application No. 60/442,161, filed on Jan. 21, 2003.

(51) Int. Cl.
*A61M 29/00* (2006.01)
(52) U.S. Cl. .......... 606/194; 604/96; 623/1.11
(58) Field of Classification Search ........ 606/159, 606/194; 604/22, 500; 623/1.11
See application file for complete search history.

(56) References Cited

U.S. PATENT DOCUMENTS

| | | | |
|---|---|---|---|
| 4,649,922 A * | 3/1987 | Wiktor | 606/194 |
| 4,838,853 A | 6/1989 | Parisi | |
| 4,887,613 A | 12/1989 | Farr et al. | |
| 4,895,166 A | 1/1990 | Farr et al. | |
| 4,921,484 A | 5/1990 | Hillstead | |
| 4,942,788 A | 7/1990 | Farr et al. | |
| 4,950,277 A | 8/1990 | Farr | |
| 4,966,604 A | 10/1990 | Reiss | |
| 4,969,458 A | 11/1990 | Wiktor | |
| 4,986,807 A | 1/1991 | Farr | |
| 4,998,539 A | 3/1991 | Delsanti | |
| 5,003,918 A | 4/1991 | Olson et al. | |
| 5,019,088 A | 5/1991 | Farr | |
| 5,019,089 A | 5/1991 | Farr | |
| 5,026,384 A | 6/1991 | Farr et al. | |
| 5,062,648 A | 11/1991 | Gomringer | |
| 5,100,423 A | 3/1992 | Fearnot | |
| 5,101,682 A | 4/1992 | Radisch, Jr. et al. | |
| 5,108,416 A | 4/1992 | Ryan et al. | |
| 5,112,345 A | 5/1992 | Farr | |
| 5,176,693 A | 1/1993 | Pannek, Jr. | |
| 5,192,291 A | 3/1993 | Pannek, Jr. | |
| 5,196,024 A | 3/1993 | Barath | |
| 5,209,727 A | 5/1993 | Radisch, Jr. et al. | |

(Continued)

FOREIGN PATENT DOCUMENTS

WO   WO 94/24946   11/1994

(Continued)

*Primary Examiner*—Michael Milano
*Assistant Examiner*—Victor X Nguyen
(74) *Attorney, Agent, or Firm*—Townsend and Townsend and Crew LLP

(57) ABSTRACT

A plaque scoring catheter comprises a catheter body having a balloon or other radially expansible shell at its distal end. A non-axial scoring structure is carried over the shell and scores a stenosed region in a blood vessel when the balloon is inflated therein. The non-axial scoring structure may be formed directly on the balloon or may alternatively be part of a cage structure which floats over the balloon. Exemplary configurations for the scoring structure include helical, serpentine, and irregular.

54 Claims, 11 Drawing Sheets

U.S. PATENT DOCUMENTS

| | | | |
|---|---|---|---|
| 5,221,261 A | 6/1993 | Termin et al. | |
| 5,224,945 A | 7/1993 | Pannek, Jr. | |
| 5,224,949 A | 7/1993 | Gomringer et al. | |
| 5,226,887 A | 7/1993 | Farr et al. | |
| 5,243,997 A | 9/1993 | Uflacker et al. | |
| 5,295,493 A | 3/1994 | Radisch, Jr. | |
| 5,295,959 A * | 3/1994 | Gurbel et al. | 604/103.13 |
| 5,308,354 A | 5/1994 | Zacca et al. | |
| 5,318,576 A | 6/1994 | Weiss et al. | |
| 5,320,634 A | 6/1994 | Vigil et al. | |
| 5,336,234 A | 8/1994 | Vigil et al. | |
| 5,344,401 A | 9/1994 | Radisch et al. | |
| 5,350,101 A | 9/1994 | Godlewski | |
| 5,376,077 A | 12/1994 | Gomringer | |
| 5,443,078 A | 8/1995 | Uflacker | |
| 5,456,667 A | 10/1995 | Ham et al. | |
| 5,470,314 A | 11/1995 | Walinsky | |
| 5,524,635 A | 6/1996 | Uflacker et al. | |
| 5,545,132 A * | 8/1996 | Fagan et al. | 604/103.08 |
| 5,556,405 A | 9/1996 | Lary | |
| 5,556,408 A | 9/1996 | Farhat | |
| 5,569,195 A * | 10/1996 | Saab | 604/103.13 |
| 5,571,086 A | 11/1996 | Kaplan et al. | |
| 5,616,149 A | 4/1997 | Barath | |
| 5,624,433 A | 4/1997 | Radisch, Jr. | |
| 5,649,941 A | 7/1997 | Lary | |
| 5,681,281 A | 10/1997 | Vigil et al. | |
| 5,697,944 A | 12/1997 | Lary | |
| 5,713,863 A | 2/1998 | Vigil et al. | |
| 5,713,913 A | 2/1998 | Lary et al. | |
| 5,735,816 A * | 4/1998 | Lieber et al. | 604/103.07 |
| 5,742,019 A | 4/1998 | Radisch, Jr. | |
| 5,746,716 A | 5/1998 | Vigil et al. | |
| 5,746,968 A | 5/1998 | Radisch, Jr. | |
| 5,779,698 A | 7/1998 | Clayman et al. | |
| 5,797,935 A | 8/1998 | Barath | |
| 5,800,450 A | 9/1998 | Lary et al. | |
| 5,873,852 A | 2/1999 | Vigil et al. | |
| 5,891,090 A | 4/1999 | Thornton | |
| 5,902,475 A | 5/1999 | Trozera et al. | |
| 5,916,166 A | 6/1999 | Reiss et al. | |
| 5,994,667 A | 11/1999 | Merdan et al. | |
| 6,036,689 A | 3/2000 | Tu et al. | |
| 6,053,913 A | 4/2000 | Tu et al. | |
| 6,071,285 A | 6/2000 | Lashinski et al. | |
| 6,071,286 A | 6/2000 | Mawad | |
| 6,077,298 A | 6/2000 | Tu et al. | |
| RE36,764 E * | 7/2000 | Zacca | 606/159 |
| 6,102,904 A | 8/2000 | Vigil et al. | |
| 6,106,548 A | 8/2000 | Roubin et al. | |
| 6,117,104 A | 9/2000 | Fitz | |
| 6,117,153 A | 9/2000 | Lary et al. | |
| 6,123,718 A | 9/2000 | Tu et al. | |
| 6,129,706 A | 10/2000 | Janacek | |
| 6,152,944 A | 11/2000 | Holman et al. | |
| 6,165,187 A | 12/2000 | Reger | |
| 6,190,356 B1 | 2/2001 | Bersin | |
| 6,210,392 B1 | 4/2001 | Vigil et al. | |
| 6,245,040 B1 | 6/2001 | Inderbitzen et al. | |
| 6,258,108 B1 | 7/2001 | Lary | |
| 6,296,651 B1 | 10/2001 | Lary et al. | |
| 6,306,151 B1 | 10/2001 | Lary | |
| 6,312,459 B1 | 11/2001 | Huang et al. | |
| 6,325,779 B1 | 12/2001 | Zedler | |
| 6,332,880 B1 * | 12/2001 | Yang et al. | 604/528 |
| 6,355,013 B1 | 3/2002 | van Muiden | |
| 6,371,961 B1 | 4/2002 | Osborne et al. | |
| 6,394,995 B1 | 5/2002 | Solar et al. | |
| 6,425,882 B1 | 7/2002 | Vigil | |
| 6,447,501 B1 | 9/2002 | Solar et al. | |
| 6,450,988 B1 | 9/2002 | Bradshaw | |
| 6,454,775 B1 | 9/2002 | Demarais et al. | |
| 6,475,233 B2 | 11/2002 | Trozera | |
| 6,475,234 B1 | 11/2002 | Richter et al. | |
| 6,517,765 B1 | 2/2003 | Kelley | |
| 6,562,062 B2 | 5/2003 | Jenusaitis et al. | |
| 6,569,180 B1 | 5/2003 | Sirhan et al. | |
| 6,605,107 B1 | 8/2003 | Klein | |
| 6,648,912 B2 | 11/2003 | Trout, III et al. | |
| 2002/0010487 A1 | 1/2002 | Demarais et al. | |
| 2002/0010489 A1 | 1/2002 | Grayzel et al. | |
| 2002/0038144 A1 | 3/2002 | Trout, III et al. | |
| 2002/0091438 A1 | 7/2002 | Trozera | |
| 2002/0165599 A1 | 11/2002 | Nasralla | |
| 2003/0018376 A1 | 1/2003 | Solar et al. | |
| 2003/0032973 A1 | 2/2003 | Jenusaitis et al. | |
| 2003/0065381 A1 | 4/2003 | Solar et al. | |
| 2003/0074046 A1 | 4/2003 | Richter | |
| 2003/0105509 A1 | 6/2003 | Jang et al. | |
| 2003/0144683 A1 | 7/2003 | Sirhan et al. | |
| 2003/0149468 A1 | 8/2003 | Wallsten | |
| 2003/0153870 A1 | 8/2003 | Meyer et al. | |
| 2003/0171799 A1 | 9/2003 | Lee et al. | |
| 2003/0195609 A1 | 10/2003 | Berenstein et al. | |
| 2003/0199970 A1 | 10/2003 | Shanley | |
| 2003/0199988 A1 | 10/2003 | Devonec et al. | |
| 2003/0208255 A1 | 11/2003 | O'Shaughnessy et al. | |
| 2006/0149308 A1 | 7/2006 | Melsheimer et al. | |
| 2006/0184191 A1 | 8/2006 | O'Brien | |

FOREIGN PATENT DOCUMENTS

| | | |
|---|---|---|
| WO | WO 98/45506 A1 | 10/1998 |
| WO | WO 02/083011 | 10/2002 |
| WO | WO 03/026536 A1 | 4/2003 |
| WO | WO 03/039628 A2 | 5/2003 |
| WO | WO 03/041760 A2 | 5/2003 |

\* cited by examiner

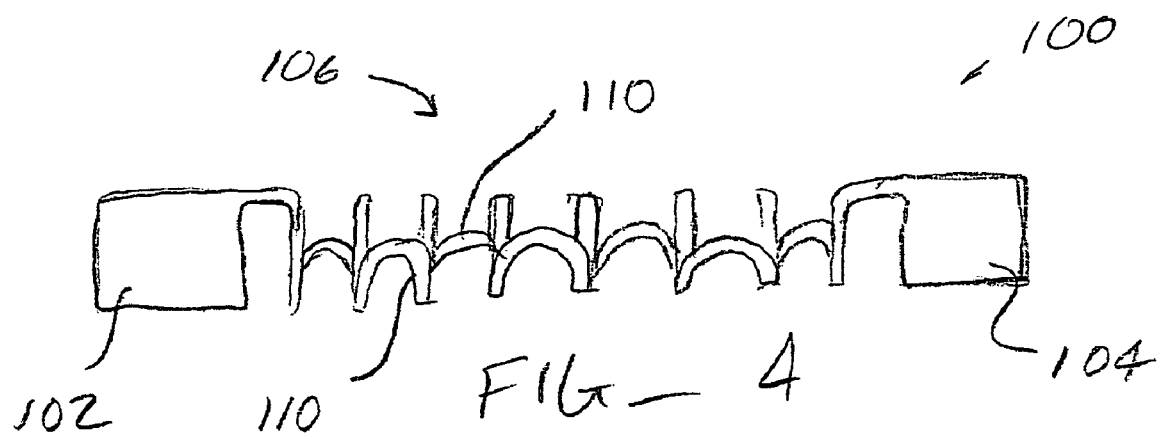
FIG_4
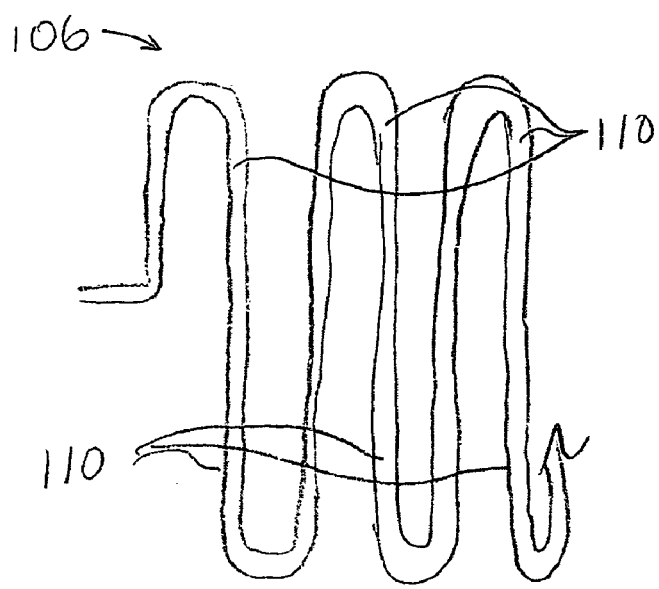
FIG_5

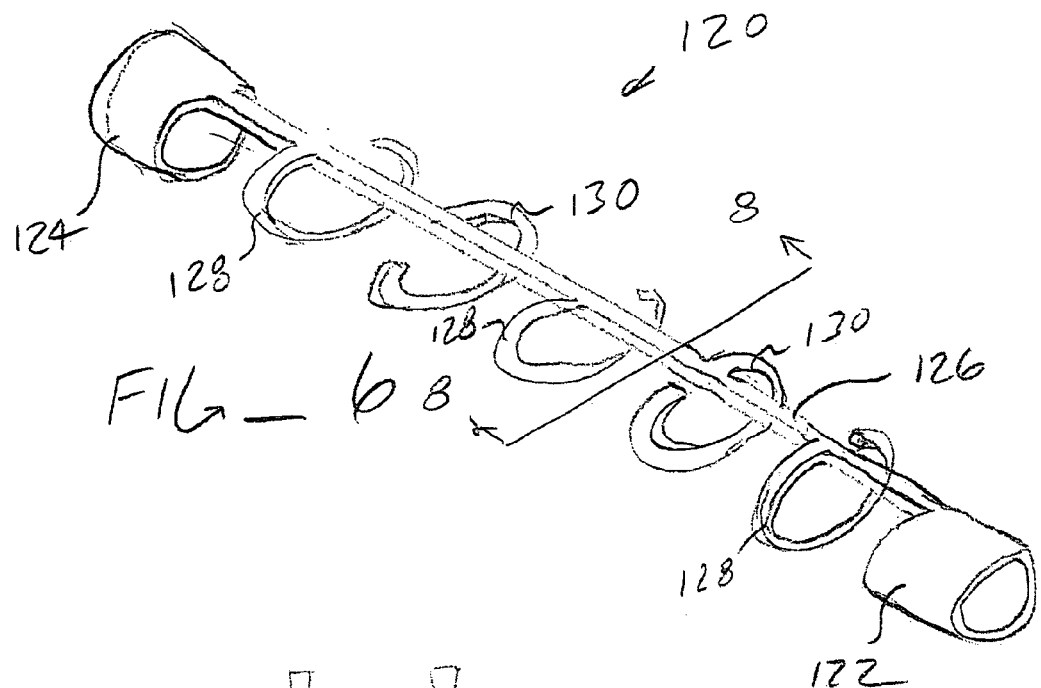
FIG_6B
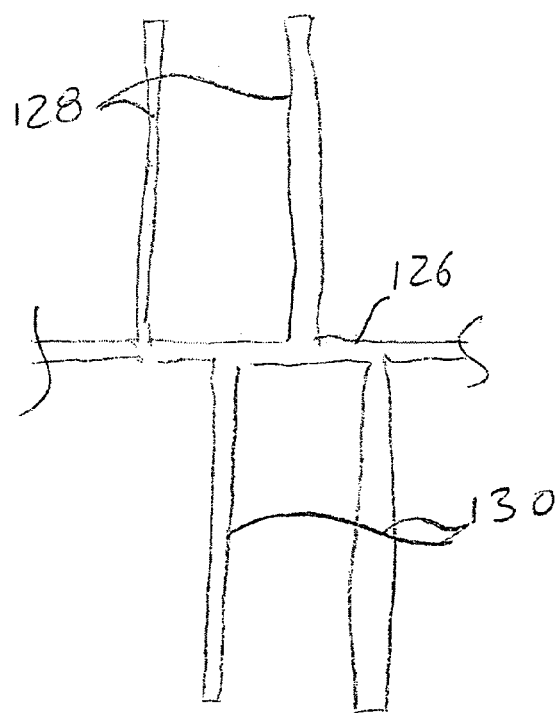
FIG_7
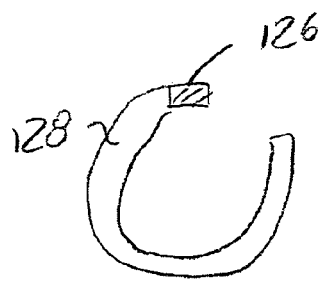
FIG_8
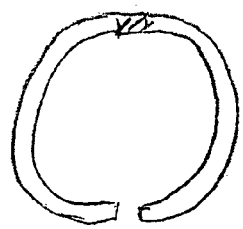
FIG_9

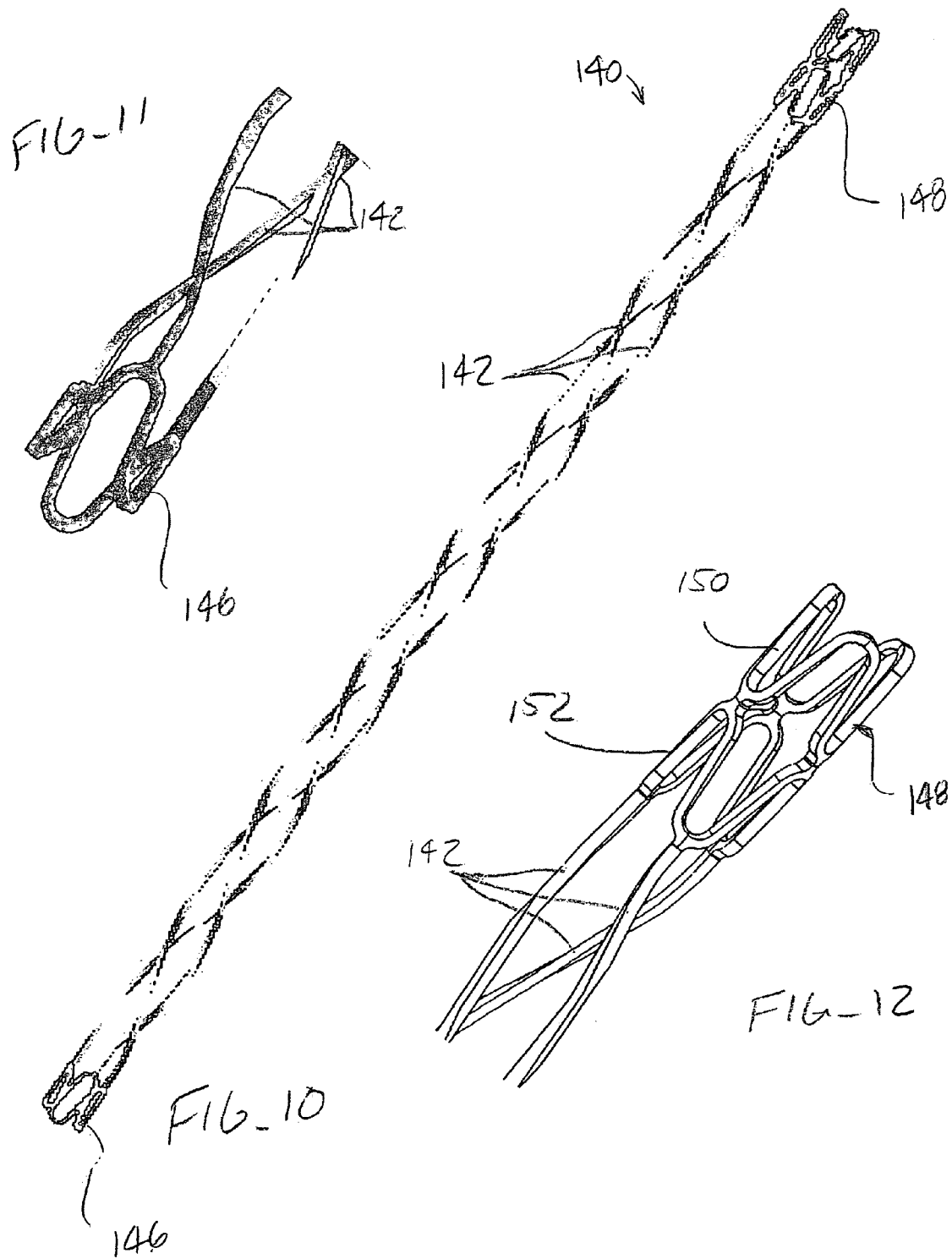

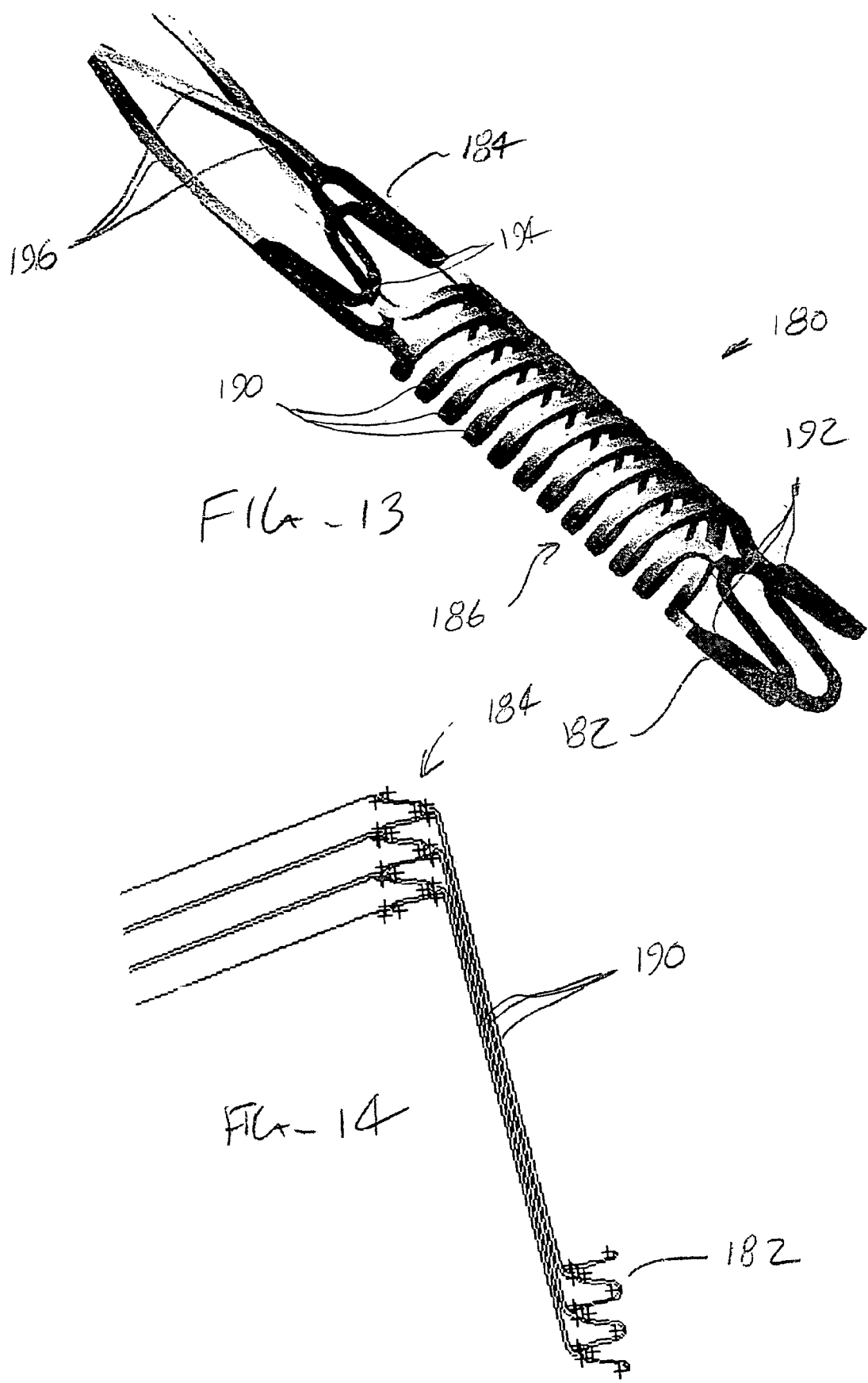

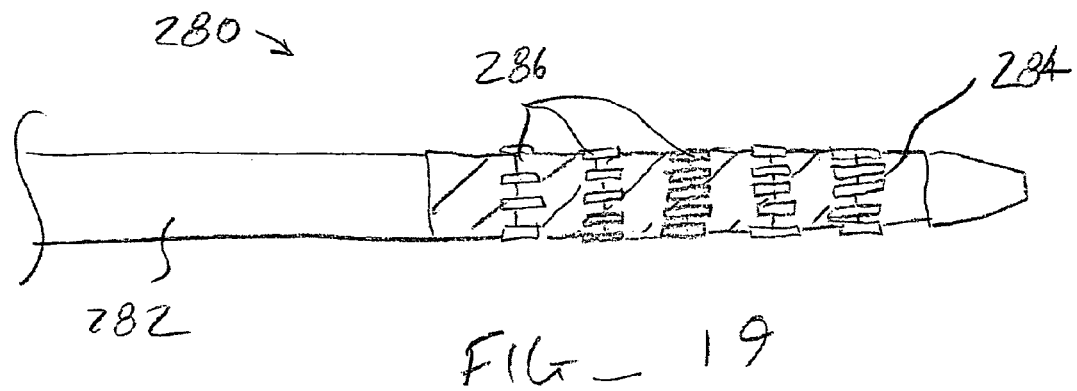
FIG_19
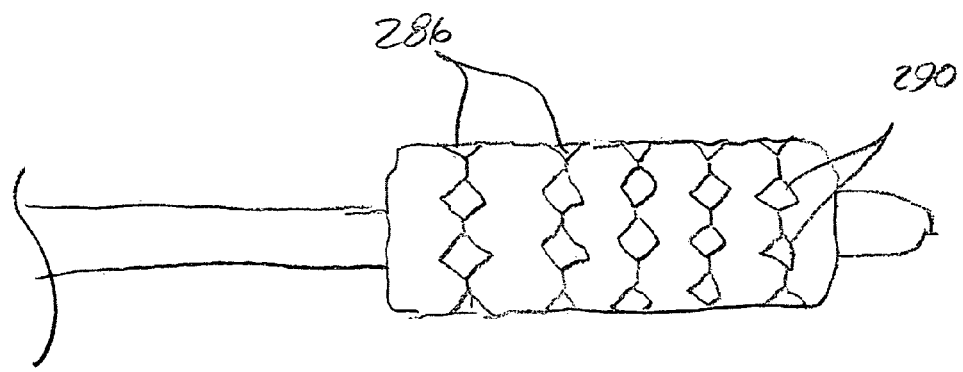
FIG_20
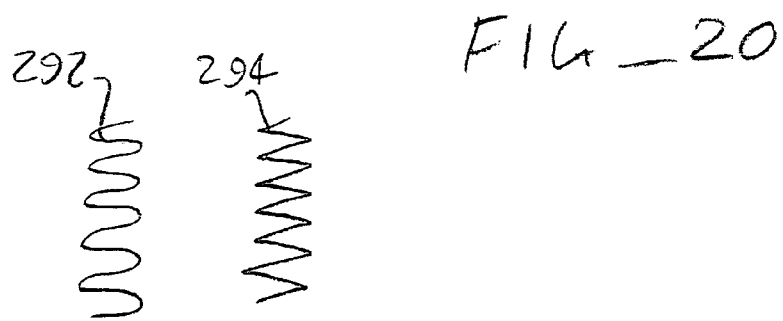
FIG_21  FIG_22

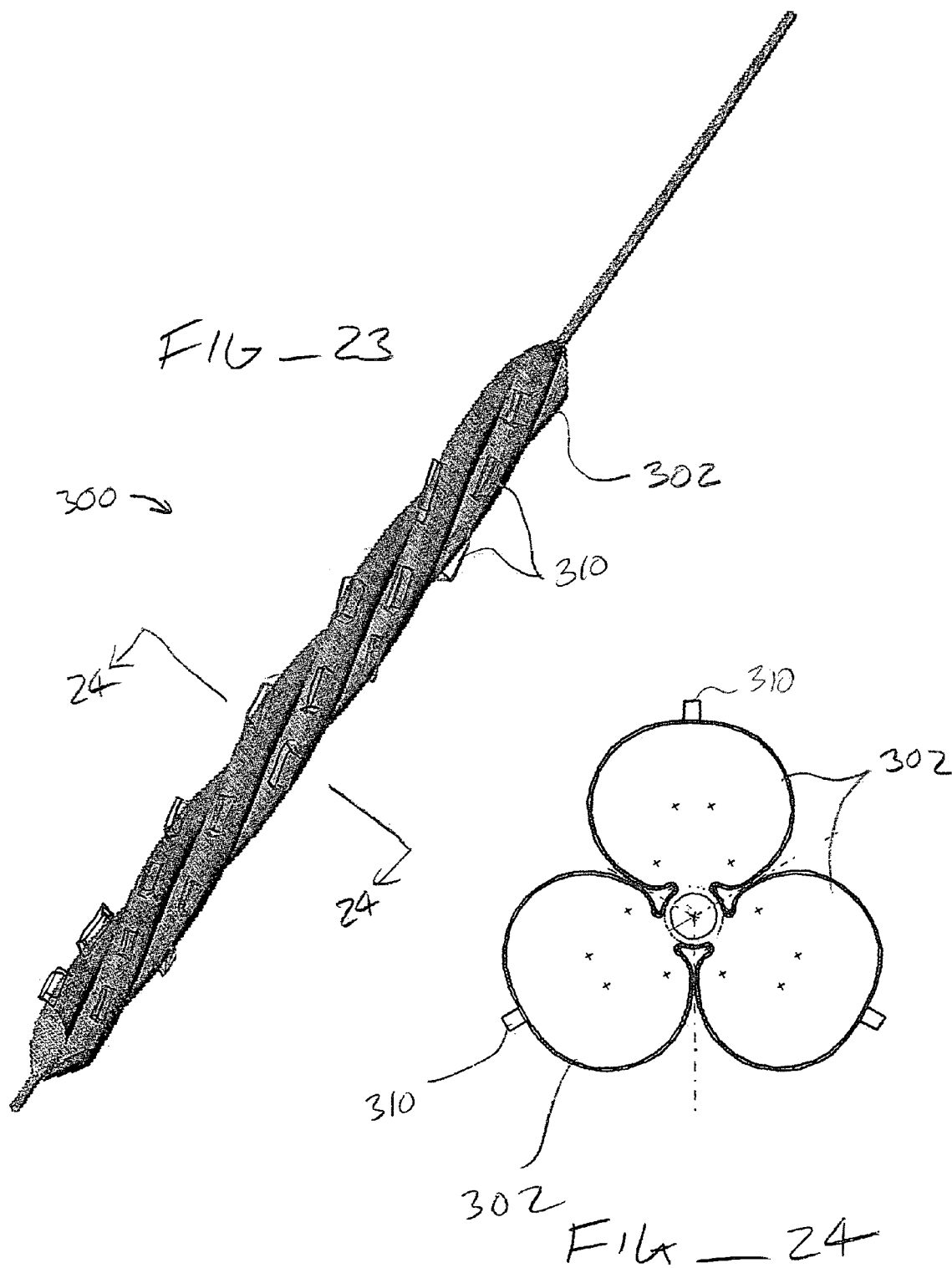

APPARATUS AND METHODS FOR TREATING HARDENED VASCULAR LESIONS

CROSS-REFERENCES TO RELATED APPLICATIONS

This application is a non-provisional of application No. 60/442,161, filed on Jan. 21, 2003, the full disclosure of which is incorporated herein by reference.

BACKGROUND OF THE INVENTION

1. Field of the Invention

The present invention relates to the field of medical devices, more specifically medical to devices intended to treat stenoses in the vascular system.

Balloon dilatation (angioplasty) is a common medical procedure mainly directed at revascularization of stenotic vessels by inserting a catheter having a dilatation balloon through the vascular system. The balloon is inflated inside a stenosed region in a blood vessel in order to apply radial pressure to the inner wall of the vessel and widen the stenosed region to enable better blood flow.

In many cases, the balloon dilatation procedure is immediately followed by a stenting procedure where a stent is placed to maintain vessel patency following the angioplasty. Failure of the angioplasty balloon to properly widen the stenotic vessel, however, may result in improper positioning of the stent in the blood vessel. If a drug-eluting stent is used, its effectiveness may be impaired by such improper positioning and the resulting restenosis rate may be higher. This is a result of several factors, including the presence of gaps between the stent and the vessel wall, calcified areas that were not treated properly by the balloon, and others.

Conventional balloon angioplasty suffers from a number of other shortcomings as well. In some cases the balloon dilatation procedure causes damage to the blood vessel due to aggressive balloon inflation that may stretch the diseased vessel beyond its elastic limits. Such over inflation may damage the vessel wall and lead to restenosis of the section that was stretched by the balloon. In other cases, slippage of the balloon during the dilatation procedure may occur. This may result in injury to the vessel wall surrounding the treated lesion. One procedure in which slippage is likely to happen is during treatment of in-stent restenosis, which at present is difficult to treat by angioplasty balloons. Fibrotic lesions are also hard to treat with conventional balloons, and elastic recoil is usually observed after treatment of these lesions. Many long lesions have fibrotic sections that are difficult to treat using angioplasty balloons.

An additional problem associated with balloon angioplasty treatment has been the "watermelon seed effect." Angioplasty is carried out at very high pressures, typically up to twenty atmospheres or higher, and the radially outward pressure of the balloon can cause axial displacement of the balloon in a manner similar to squeezing a watermelon seed with the fingers. Such axial displacement, of course, reduces the effectiveness of balloon dilatation. Another problem with conventional angioplasty balloon design has been deflation of the balloon. Even after the inflation medium is removed from a balloon, the deflated configuration will have a width greater than the original folded configuration which was introduced to the vasculature. Such an increase in profile can make removal of the balloon difficult.

To overcome at least some of these problems these problems, U.S. Pat. No. 5,320,634 describes the addition of cutting blades to the balloon. The blades can cut the lesions as the balloon is inflated. U.S. Pat. No. 5,616,149 describes a similar method of attaching sharp cutting edges to the balloon. U.S. Patent Publication 2003/0032973 describes a stent-like structure having non-axial grips for securing an angioplasty balloon during inflation. U.S. Pat. No. 6,129,706 describes a balloon catheter having bumps on its outer surface. U.S. Pat. No. 6,394,995 describes a method of reducing the balloon profile to allow crossing of tight lesions.

While the use of angioplasty balloons having cutting blades has proved to be a significant advantage under many circumstances, the present cutting balloon designs and methods for their use continue to suffer from shortcomings. Most commercial cutting balloon designs, including those available from InterVentional Technologies, Inc., San Diego, Calif., now owned by Boston Scientific, Natick, Mass., have relatively long, axially aligned blades carried on the outer surface of an angioplasty balloon. Typically, the blades are carried on a relatively rigid base directly attached to the outer balloon surface. The addition of such rigid, elongated blade structures makes the balloon itself quite stiff and limits the ability to introduce the balloon through torturous regions of the vasculature, particularly the smaller vessels within the coronary vasculature. Moreover, the cutting balloons can be difficult to deflate and collapse, making removal of the balloons from the vasculature more difficult than with corresponding angioplasty balloons which do not include cutting blades. Additionally, the axially oriented cuts imparted by such conventional cutting balloons do not always provide the improved dilatation and treatment of fibrotic lesions which would be desired.

For these reasons, it would be desirable to provide improved cutting balloon designs and methods for their use. In particular, it would be desirable to provide cutting balloons which are highly flexible over the length of the balloon structure, which readily permit deflation and facilitate removal from the vasculature, and which are effective in treating all forms of vascular stenoses, including but not limited to treatment of highly calcified plaque regions of diseased arteries, treatment of small vessels and/or vessel bifurcations that will not be stented, treatment of ostial lesions, and treatment of in-stent restenosis (ISR). Moreover, it would be desirable if such balloon structures and methods for their use could provide for improved anchoring of the balloon during dilatation of the stenosed region. At least some of these objectives will be met with the inventions described hereinafter.

2. Description of the Background Art

The following U.S. patents and printed publication relate to cutting balloons and balloon structures: 6,450,988; 6,425,882; 6,394,995; 6,355,013; 6,245,040; 6,210,392; 6,190,356; 6,129,706; 6,123,718; 5,891,090; 5,797,935; 5,779,698; 5,735,816; 5,624,433; 5,616,149; 5,545,132; 5,470,314; 5,320,634; 5,221,261; 5,196,024; and Published U.S. Pat. App. 2003/0032973. Other U.S. Pat. Nos. of interest include 6,454,775; 5,100,423, 4,998,539; 4,969,458; and 4,921,984.

SUMMARY OF THE INVENTION

The present invention provides improved apparatus and methods for the dilatation of stenosed regions in the vasculature. The stenosed regions will often include areas of fibrotic, calcified, or otherwise hardened plaque or other stenotic material of the type which can be difficult to dilatate using conventional angioplasty balloons. The methods and apparatus will often find their greatest use in treatment of the arterial vasculature, particularly the coronary arterial vasculature, but may also find use in treatment of the venous and/or peripheral vasculature, treatment of small vessels and/or vessel bifurcations that will not be stented, treatment of ostial lesions, and treatment of ISR.

In a first aspect of the present invention, a scoring catheter comprises a catheter body having a proximal end and a distal end, a radially expansible shell near the distal end of the catheter body, and a non-axial scoring structure carried over the shell. By "non-axial scoring structure," it is meant that the structure will be able to score or cut stenotic material within a treated blood vessel along lines which are generally in a non-axial direction. For example, the scoring lines may be helical, serpentine, zig-zag, or may combine some axial components together with such non-axial components. Usually, the non-axial scoring pattern which is imparted will include scoring segments which, when taken in total, circumscribe at least a majority of and usually the entire inside wall of the blood vessel at least one time, preferably more than one time, usually more than two times, often at least three times, more often at least four, five, six, or more times. It is believed that the resulting scoring patterns which circumscribes the inner wall of the vessel will provide improved results during subsequent balloon dilatation.

Usually the scoring structure will comprise at least one continuous, i.e., non-broken, scoring element having a length of at least 0.5 cm, more usually at least 1 cm, often at least 2 cm, usually at least 3 cm, and sometimes at least 4 cm or more. Alternatively, the scoring structure may comprise a plurality of much smaller segments which may be arranged in a helical or other pattern over the balloon, typically having a length in the range from 0.1 cm to 2 cm, often being 0.5 cm or less, sometimes being 0.3 cm or less.

In order to promote scoring of the blood vessel wall when the underlying expansible shell is expanded, the scoring structure will usually have a vessel contact area which is 20% or less of the area of the expansible shell, usually being below 10%, and often being in the range from 1% to 5% of the area of the expansible shell. The use of a shell having such a relatively small contact area increases the amount of force applied to the vascular wall through the structure by expansion of the underlying expandable shell. The scoring structure can have a variety of particular configurations, often being in the form of a wire or slotted tube having a circular, square, or other cross-sectional geometry. Preferably, the components of the scoring structure will comprise a scoring edge, either in the form of a honed blade, a square shoulder, or the like. A presently preferred scoring edge is electropolished and relatively small.

In a preferred embodiment, the scoring structure may be formed as a separate expansible cage which is positioned over but unattached to the expansible shell of the catheter. The cage will usually have a collar or other attachment structure at each end for placement on the catheter body on either side of the expansible shell. A collar may be a simple tube, and other attachment structures will usually be crimpable or otherwise mechanically attachable to the catheter body, such as a serpentine or other ring structure. The attachment structures on the cage may be attached at both ends to the catheter body, but will more usually be attached at only a single end with the other end being allowed to float freely. Such freedom allows the scoring structure to shorten as the structure is expanded on the expansible shell. In certain embodiments, both ends of the scoring structure will be fixed to the catheter body, but at least one of the attachment structures will have a spring or other compliant attachment component which provides an axial extension as the center of the scoring structure foreshortens.

In many cases, since the scoring elements are non-axial, there are torques induced during the expansion of the balloon and the shortening of the scoring structure. These torques may be high, and if one end of the scoring structure is constrained from rotation, the scoring element will not expand properly. The final expanded configuration of the scoring element is achieved via shortening and rotation.

In a preferred embodiment, both sides of the scoring element are fixed to the catheter, but at least one side will have a compliant structure which will provide axial tension and at the same time will allow the scoring element to rotate to its final configuration.

In some cases both ends of the scoring element are fixed and the shortening is achieved by deformation of the wire. For example, the wire can have a secondary structure which permits elongation (e.g., it may be a coiled filament) or can be formed from a material which permits elongation, e.g., nitinol. The scoring element can be attached in both ends, in a way that will allow rotation. In the case were the torques are low (depending on the design of the scoring element) there is no need for rotation and the torque can be absorbed either be the scoring element of by the catheter.

In all cases, the scoring structure is preferably composed of an elastic material, more preferably a super elastic material, such as nitinol. The scoring structure is thus elastically expanded over the expansible shell, typically an inflatable balloon similar to a conventional angioplasty balloon. Upon deflation, the scoring structure will elastically close to its original non-expanded configuration, thus helping to close and contain the balloon or other expandable shell.

In some cases the scoring element will be a combination of more than one material. In one case the scoring element can be made from nitinol and parts of it can be made from stainless steel. In other cases the scoring element can be made of stainless steel or nitinol and part of it can be made from polymer to allow high deformations.

In other preferred embodiments, the assembly of the shell and the scoring structure will be sufficiently flexible to permit passage through tortuous regions of the vasculature, e.g., being capable of bending at radius of 10 mm or below when advanced through 45°, 90° or higher bends in the coronary vasculature. Usually, the scoring structure will comprise one or more scoring elements, wherein less than 70% of the cumulative length of the scoring element is aligned axially on the shell when expanded, preferably being less than 50% of the cumulative length, and more preferably being less than 25% of the cumulative length. In other instances, the scoring structure may comprise one or more scoring elements, wherein the cumulative length of the scoring element includes a non-axial component of at least 10 mm, preferably at least 12 mm, and more preferably 36 mm. Preferably, at least some of the scoring elements will have scoring edges which are oriented radially outwardly along at least a major portion of their lengths at all times during inflation and deflation and while inflated. By "radially outward," it is meant that a sharp edge or shoulder of the element will be oriented to score or cut into the stenotic material or the interior wall of the treated vessel, particularly as the shell is being inflated.

The scoring elements will usually, but not necessarily, have a scoring edge formed over at least a portion of their lengths. A "scoring edge" may comprise a sharpened or honed region, like a knife blade, or a square shoulder as in scissors or other shearing elements. Alternatively, the scoring elements may be free from defined scoring edges, e.g., having circular or the other non-cutting profiles. Such circular scoring elements will concentrate the radially outward force of the balloon to cause scoring or other disruption of the plaque or other stenotic material being treated.

In a second aspect of the present invention, the scoring catheter comprises a catheter body and a radially expansible shell, generally as set forth above. The scoring structure will be composed of elements which circumscribe the radially expansible shell. By "circumscribing the radially expansible shell," it is meant that at least some scoring elements of the scoring structure will form a continuous peripheral path about the exterior of the expansible shell during expansion. An example of such a fully circumscribing structure is a helical structure which completes at least one 360° path about the balloon before, during and after expansion, usually completing two complete revolutions, and frequently completing three, four, or more complete revolutions. Exemplary helical structures may include two, three, four, or more separate elements, each of which is helically arranged around the radially expansible shell.

In a third aspect of the present invention, a scoring catheter comprises a catheter body and a radially expansible shell, generally as set forth above. An elongated scoring structure is carried over the shell, and the assembly of the shell and the scoring structure will be highly flexible to facilitate introduction over a guide wire, preferably being sufficiently flexible when unexpanded so that it can be bent at an angle of at least 90°, preferably 180°, at a radius of 1 cm without kinking or otherwise being damaged. Such flexibility can be determined, for example, by providing a solid cylinder having a radius of 1 cm and conforming the assembly of the scoring structure and expansible shell over the cylinder. Alternatively, the assembly can be advanced over a guide wire or similar element having a 180° one centimeter radius bend. In either case, if assembly bends without kinking or other damage, it meets the requirement described above. Other specific features in this further embodiment of the catheters of the present invention are as described above in connection with the prior embodiments.

In a fourth aspect of the present invention, a plaque scoring catheter comprises a catheter body and a radially expansible balloon, generally as set forth above. A plurality of scoring elements are distributed over the balloon, typically being attached directly to an outer surface of the balloon. The scoring elements will be relatively short, typically having lengths below about 25% of the balloon length, preferably having lengths in the range from 2% to 10% of the balloon length. The relatively short, segmented scoring elements will permit highly flexible assemblies of balloon and scoring elements, generally meeting the flexibility requirement set forth above. The scoring elements may be arranged randomly over the balloon but will more usually be distributed uniformly over the balloon. In specific embodiments, the scoring elements may be arranged in helical, serpentine, or other regular patterns which circumscribe the balloon. As the balloon expands, such short segments will generally move apart from each other, but will still impart the desired scoring patterns into the vascular wall as the balloon is inflated.

In a fifth embodiment, the scoring catheter according to the present invention comprises a catheter body and a radially expansible balloon generally as set forth above. The balloon has a plurality of lobes extending between ends of the balloons, and at least one scoring element will be formed on at least one of the lobes in a manner arranged to score stenotic material as the balloon is expanded. The lobe will usually be in a helical pattern, and typically two, three, or more lobes will be provided. In the case of helical lobes, the scoring element(s) will usually be disposed along a helical peak defined by the helical lobe when the balloon is inflated. Such helical scoring elements will be arranged to accommodate balloon inflation, typically being stretchable, segmented, or the like.

In still another aspect of the apparatus of the present invention, an expansible scoring cage is adapted to be carried over a balloon of a balloon catheter. The scoring cage comprises an assembly of one or more elongate elastic scoring elements arranged in a non-axial pattern. As defined above, the non-axial pattern may comprise both axial and non-axial segments. The assembly is normally in a radially collapsed configuration and is expansible over a balloon to a radially expanded configuration. After the balloon is deflated, the assembly returns to a radially collapsed configuration, preferably being assisted by the elastic nature of the scoring cage. Advantageously, the scoring cage will enhance uniform expansion of the underlying balloon or other expansible shell and will inhibit "dog boning" where an angioplasty balloon tends to over inflate at each end, increasing the risk of vessel dissection. The scoring elements will be adapted to score hardened stenotic material, such as plaque or fibrotic material, when expanded by the balloon in a blood vessel lumen. The scoring cage may be adapted to mount over the balloon with either or both ends affixed to the balloon, generally as described above in connection with prior embodiments. Preferred geometries for the scoring elements include those which circumscribe the balloon, those which are arranged helically over the balloon, those which are arranged in a serpentine pattern over balloon and the like.

In yet another aspect of the present invention, a method for dilatating a stenosed region in a blood vessel comprises radially expanding a shell which carries a scoring structure. The scoring structure scores and dilates the stenosed region and includes one or more non-axial scoring elements arranged to impart a circumscribing score pattern about the inner wall of the blood vessel as the shell is expanded. The stenosed region is typically characterized by the presence of calcified plaque, fibrotic plaque, or other hardened stenotic material which is preferably scored prior to dilatation. Preferably, the scoring structure will not be moved in axial direction while engaged against the stenosed region, and the scoring structure may optionally be free from axially scoring elements.

BRIEF DESCRIPTION OF THE DRAWINGS

FIG. 4 illustrates a scoring structure comprising an alternating serpentine pattern of intermediate scoring elements between a pair of end collars.

FIG. 5 illustrates the serpentine scoring elements of the embodiment of FIG. 4 showed in a rolled-out configuration.

FIG. 6 illustrates a scoring structure comprising alternating C-shaped scoring elements between a pair of end collars.

FIG. 7 illustrates the C-shaped scoring elements of the embodiment of FIG. 6 shown in a rolled-out configuration.

FIG. 8 is a view of one of the C-shaped scoring elements taken along line 8-8 of FIG. 6.

FIG. 9 illustrates an alternative double C-shaped scoring element which could be utilized on a scoring structure similar to that illustrated in FIG. 6.

FIG. 10 illustrates an alternative embodiment of a helical scoring structure comprising serpentine and zigzag structures for mounting onto a balloon catheter.

FIG. 11 illustrates a first of the serpentine mounting elements of the scoring structure of FIG. 10.

FIG. 12 illustrates a second of the serpentine mounting elements of the scoring structure of FIG. 10.

FIG. 13 illustrates an alternative mounting structure for a helical or other scoring structure.

FIG. 14 illustrates the mounting structure of FIG. 13 shown in a rolled-out configuration.

FIG. 19 illustrates yet another alternative embodiment of the catheter constructed in accordance with the principles of the present invention shown with a ring-like scoring structure attached directly to the outer surface of the balloon.

FIG. 20 illustrates the catheter of FIG. 19 shown with the balloon in its inflated configuration.

FIGS. 21 and 22 illustrates alternative ring structures which could be incorporated in the catheter of FIG. 19.

FIG. 23 illustrates a helically lobed balloon structure having scoring segments mounted on the helical peak of each balloon lope.

FIG. 24 is a cross-sectional view of the balloon catheter of FIG. 23 taken along line 24-24.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Embodiments of the present invention relate to device for revascularization of stenotic vessels and specifically to a balloon catheter having external elements. The dilatation device comprises a conventional dilatation balloon such as a polymeric balloon and a spiral, or external elements with other configurations mounted on the balloon catheter.

Figure 1:
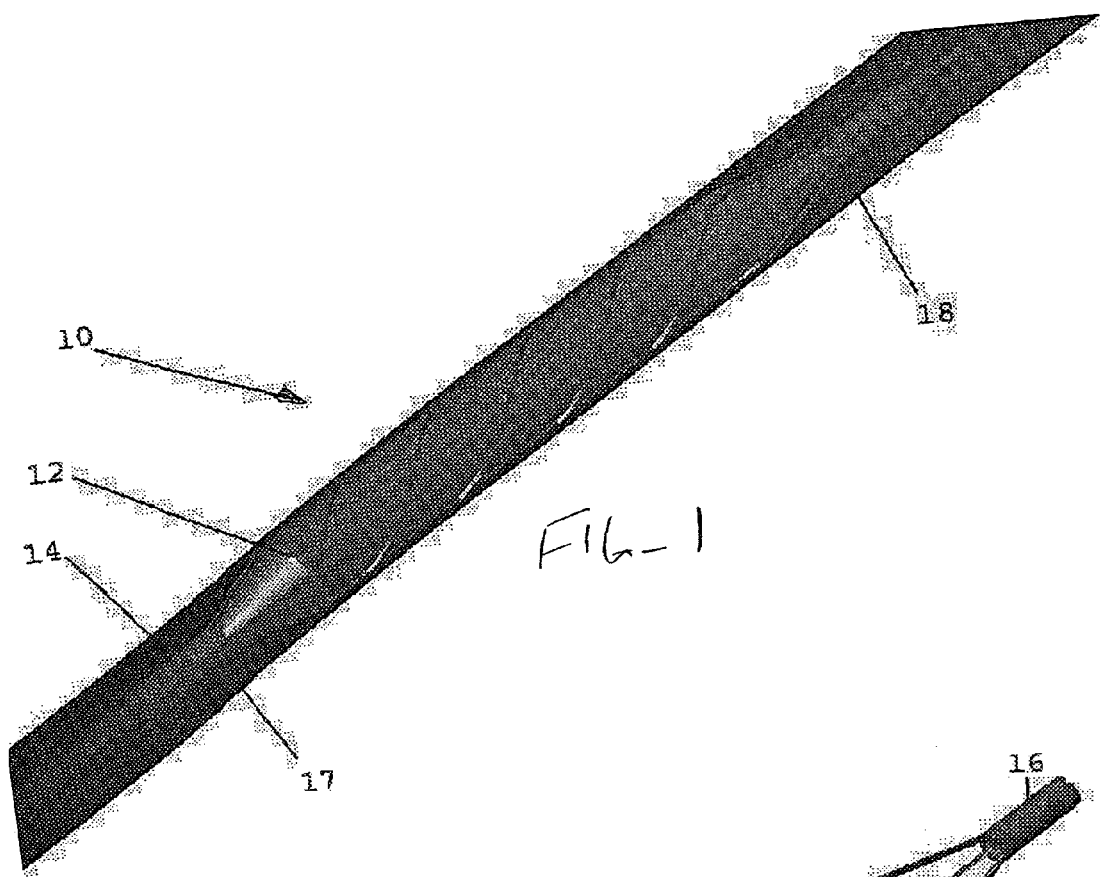
FIGS. 1, 1A, 1B and 1C are schematic illustrations of the balloon scoring structure embodiment in accordance with an embodiment of the invention.
Figure 1A:
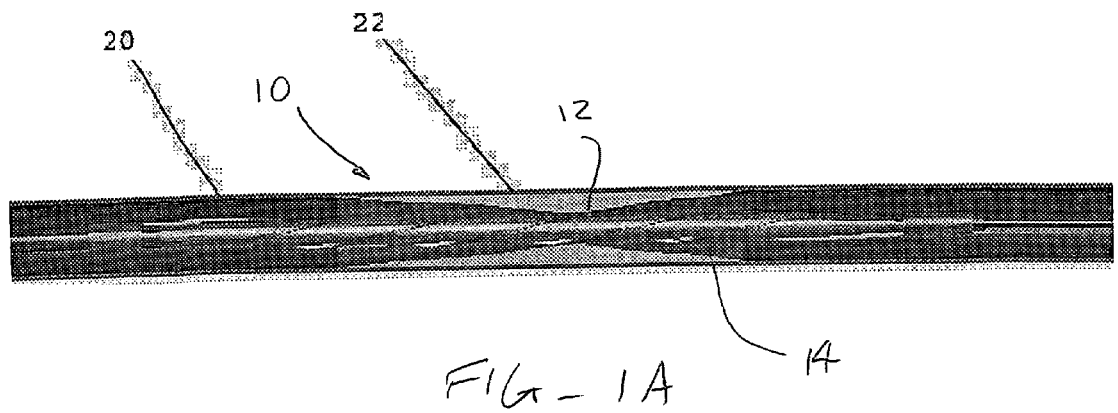
Figure 1B:
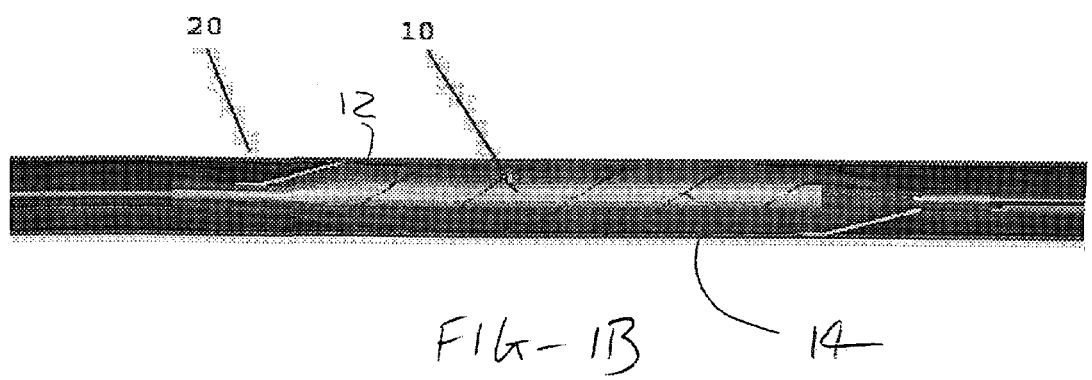

Reference is now made to FIGS. 1, 1A and 1B, which are schematic illustrations of a dilatation device 10 in accordance with embodiments of the invention. The dilatation device 10 includes a dilatation balloon 12, which may be any conventional angioplasty balloon such as commonly used by interventional cardiologists or radiologists, and a helical or spiral unit 14 mounted over or attached to dilatation balloon 12. The compliance of the balloon and the scoring element(s) should be chosen to assure uniform expansion of the balloon substantially free from "dog-boning" as the combined structure expands within a lesion. If a compliant or a semi-compliant balloon is used and the compliance of the scoring element was not matched to comply with the properties of the balloon, the expansion of the balloon-scoring element system will not be uniform. This non-uniformity may impair the efficacy of the scoring catheter and, in some cases, may result in poor performance. For example, under given pressure, certain parts of the balloon will be able to expand while other parts will be constrained by excessive resistance of the scoring elements.

Helical unit 14 typically made of nitinol. Helical unit 14 may be made of other metals such stainless steel, cobalt-chromium alloy, titanium, and the like. Alternatively, spiral unit 14 may be a polymeric spiral, or made of another elastic material. Helical unit 14 may be attached at its proximal and distal ends to the proximal end 17 and distal end 18 of dilatation balloon 12. Alternatively, spiral unit 14 may be attached to the distal end and/or the proximal end of dilatation balloon 12 by collar-like attachment elements 15 and 16. Spring or other compliant elements may be alternatively or additionally provided as part of the attachment elements to accommodate shortening of the helical unit as it is expanded.

Dilatation device 10 is inserted into the vascular system, for example, using a conventional catheter procedure, to a region of stenotic material 22 of blood vessel 20. (The term "stenotic" is used herein to refer to the vascular lesion, e.g., the narrowed portion of the vessel that the balloon is meant to open.) At the stenotic area, the dilatation balloon 12 is inflated, for example, by liquid flow into the balloon. Helical unit 14 widens on the inflated dilatation balloon 12. On inflation, the dilatation balloon 12 together with the helical unit 14 is pressed against the walls of blood vessel 20 as shown in FIG. 1B.

Figure 1C:
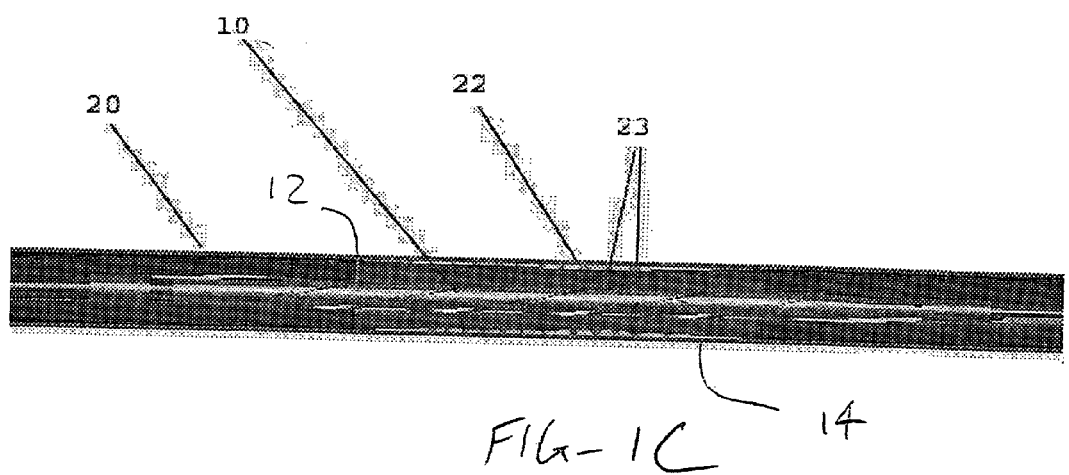

Reference is now made to FIG. 1C, illustrating blood vessel 20 after the deflation of dilatation balloon 12. Helical unit 14 narrows when deflating the dilatation balloon 12, thus the dilatation device 10 is narrowed and may be readily retrieved from blood vessel 20. The deflation profile of the balloon 10 is low and mainly circular. The stenotic material 22 in blood vessel 20 is pressed against blood vessel 20 walls to widen the available lumen and enhance blood flow. The pressing of helical unit 14 against the walls of blood vessel 20 causes scoring 23 in the stenotic area.

Figure 3:
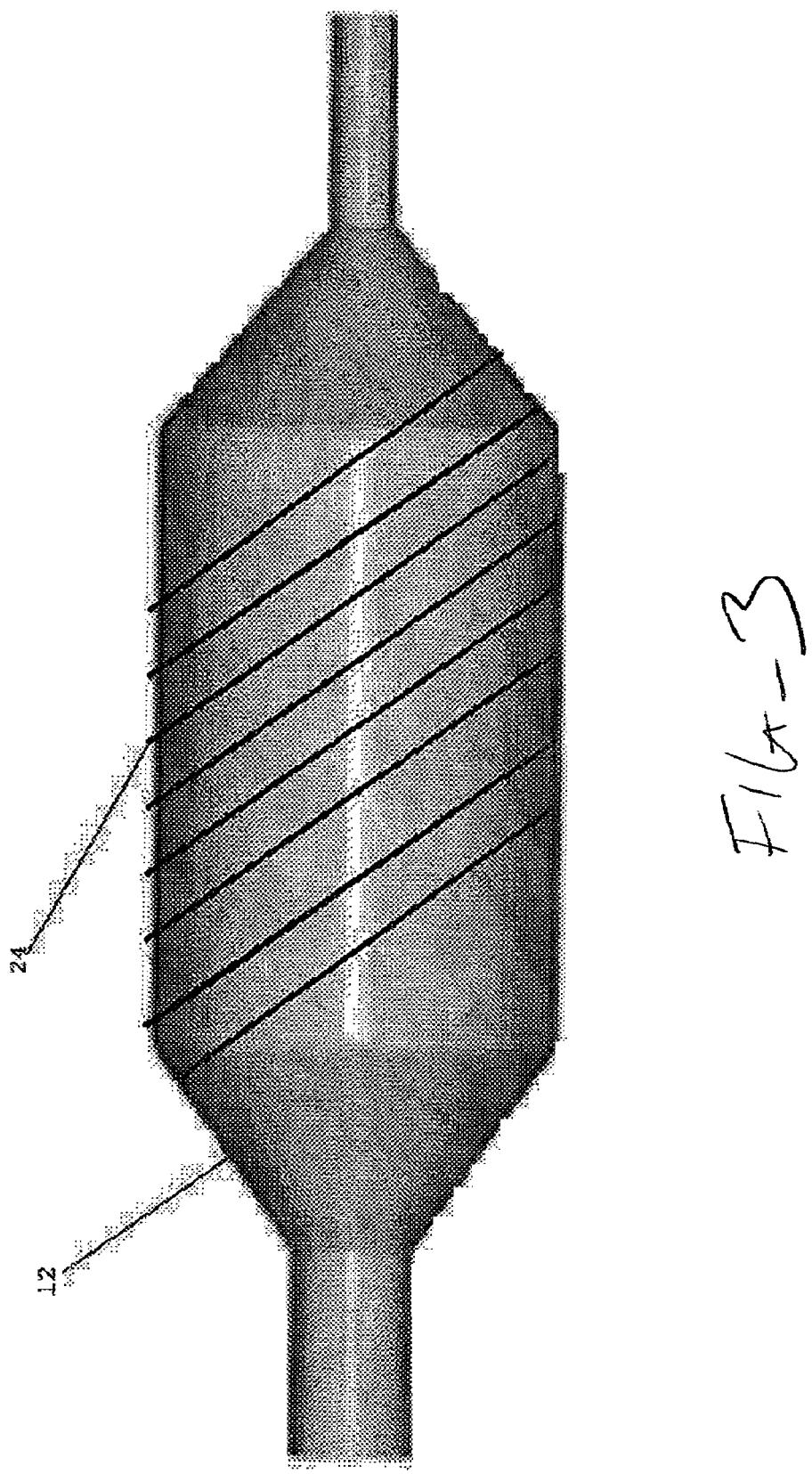
FIG. 3 is a schematic illustration of an expanded angioplasty balloon carrying a helical scoring structure in accordance with embodiments of the invention.

Reference is now made to FIG. 3 that shows a scoring structure in the form of a single wire 24 wrapped around a dilatation balloon 12 in a helical configuration.

In other embodiments, the scoring structure of the present invention can have a non-helical configuration. Any design of scoring structure that can accommodate an increase in the diameter of the balloon 12 upon inflation, and return to its configuration when the balloon is deflated, is an appropriate design useful in the invention. At least a portion of the scoring elements will not be parallel to the longitudinal axis of the balloon catheter to enhance flexibility and improve scoring.

Referring again to FIGS. 1A-1C, helical unit 14 is pushed outwardly by the inflation of the balloon 12, and is stretched by the inflation of the balloon. When the balloon is deflated, helical unit 14 assists in the deflation by its elastic recoil. This active deflation is faster and also leads to a low profile of the deflated balloon. The balloon 12 is disposed within the helical unit 14, which returns to its pre-inflated shape and forces the balloon to gain a low radial profile.

In another embodiment of the invention, dilatation device 10 may carry a stent. The stent can be crimped over the helical unit 14. In this way, the helical unit 14 can push the stent against hard areas of the lesion, enabling proper positioning of the stent against the vessel wall, even in hard-calcified lesions without pre-dilation.

Figure 2:
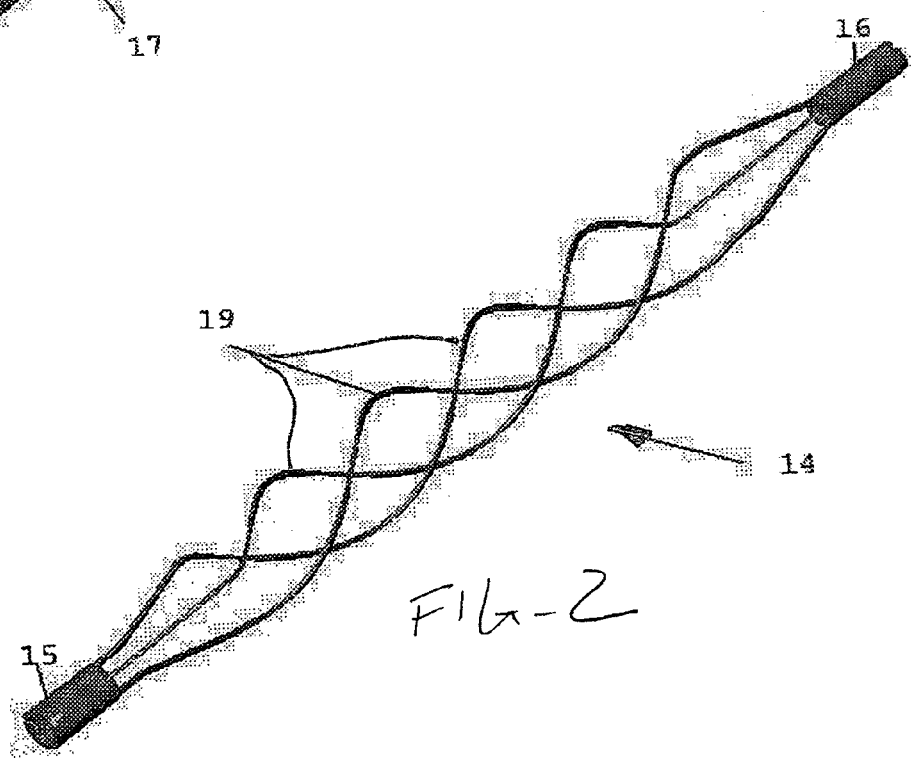
FIG. 2 is a schematic illustration of an exemplary helical scoring structure embodiment in accordance with embodiments of the invention.

Reference is now made to FIG. 2, illustrating the helical unit 14 in accordance with embodiments of the invention. Helical unit 14 is typically made of nitinol. Helical unit 14 includes three wires 19 that are attached to collars 15 and 16 at the proximal end and distal end, respectively. Alternatively the scoring structure may be formed as a metallic cage, which can be made from a slotted tube, or polymeric cage or polymeric external elements. Alternatively the scoring structure may comprise wires of other elements attached directly to the balloon material or close to the balloon ends.

Wires 19 (FIG. 2) are attached between collars 14 and 15. The diameter of the wires is typically in the range of 0.05 mm to 0.5 mm. Alternatively, a cage (for example a metallic cage made of a slotted tube) can be used in several configurations that allow local stress concentrations. The size and shape of the cross section of the cage elements or the cross section of the wires can vary. The cross section can be a circle, rectangle, triangle, or other shape.

In alternative embodiments, the wires 19 may comprise short segments that are attached to the balloon 12.

In further alternative embodiments of the invention, the helical unit 14 may be glued, thermally bonded, fused or mechanically attached at one or both ends to dilatation balloon 12.

In yet another embodiment, a scoring structure may comprise wires that are attached to the dilatation balloon 12 in helical configuration or other configuration. The wires may be thermally attached to the balloon 12, glued, mechanically attached, or the like.

In still another embodiment, a scoring structure comprises wire or cage elements that are not parallel to the longitudinal axis of the balloon 12 so that the combination of the scoring structure 19 and the balloon 12 remains flexible.

In additional embodiments, the combination of dilatation balloon 12 and scoring structure scores the lesion and provides better vessel preparation for drug eluting stents by allowing better positioning of the stent against the vessel wall and diffusion of the drug through the scores in the lesion.

In these embodiments, the balloon can be used as a platform to carry drugs to the lesion where scoring of the lesion can enhance delivery of the drug to the vessel wall.

In these embodiments, the balloon can be used for a local drug delivery by embedding drug capsules, drug containing polymer, and the like, through the stenotic material and into the vessel wall.

From the above, it can be seen that the invention comprises catheters and scoring structures, where the scoring structures are positioned over the balloons or other expansible shells of the catheter. The scoring structures may be attached directly to the balloons or other shells, in some cases being embedded in the balloon material, but will more usually be formed as separate cage structures which are positioned over the balloon and attached to the catheter through attachment elements on either side of the balloon. The expansible cages may be formed using conventional medical device fabrication techniques, such as those used for fabricating stents, such as laser cutting of hypotube and other tubular structures, EDM forming of hypotubes and tubes, welding of wires and other components and the like.

Typically, such expansible shell structures will comprise the attachment elements and an intermediate scoring section between the attachment elements. As illustrated in the embodiments above, the attachment elements may be simple cylindrical or tube structures which circumscribe the catheter body on either side of the balloon or other expansible shell. The simple tube structures may float over the catheter body, i.e., be unattached, or may be fixed to the catheter body. A number of alternative embodiments for the attachment elements will be described in connections with the embodiments below.

The intermediate scoring sections may also have a variety of configurations where at least some of the scoring elements will typically be disposed in a non-axial configuration, i.e., in a direction which is not parallel to the axial direction of the expansible cage. A preferred configuration for the intermediate scoring section comprises one or more helical elements, generally as illustrated in the prior embodiments. Other exemplary configurations are set forth in the embodiments described below.

Referring now in particular to FIGS. 4 and 5, an expansible scoring cage 100 comprises first and second attachment elements 102 and 104, respectively, and an intermediate scoring section 106 comprising a plurality of curved serpentine members 110. The serpentine members 110 extend circumferentially in opposite directions in an alternating manner. This can be understood by observing a "rolled-out" view of the serpentine elements as illustrated in FIG. 5. A second alternative scoring cage structure 120 is illustrated in FIGS. 6-8. The scoring cage 120 comprises first and second attachment elements 122 and 124 joined by a spine 126. Plurality of C-shaped scoring elements 128 and 130 are attached to the spine and extend in opposite circumferential directions. The shape of the element can be observed in FIG. 8. The opposite directions may be observed in the rolled-out view of FIG. 7.

It will be appreciated that a variety of different circumferential structures may be used in place of the C-shaped structures of FIGS. 6-8. For example, a pair of opposed C-shaped partial ring structures may be utilized, as illustrated in FIG. 9. The C-shaped structures of FIG. 6 or the double C-shaped structures of FIG. 9 can also be extended so that they wrap around a balloon more than one time, either over or under the spine structure 126.

The expansible cage structures 100 and 120 will each be mounted over a dilatation balloon, such as the balloon of FIGS. 1-3, with the attachment elements secured to the catheter body on either side of the dilatation balloon. The tube or cylindrical attachment elements 102, 104, 122, and 124 may simply float over the catheter body. In other embodiments, however, it may be desirable to use an adhesive or other means for affixing either one or both of the attachment elements to the catheter body. Having at least one floating attachment element, however, is often desirable since it can accommodate shortening of the intermediate scoring section as that section radially expands. In other cases, however, the individual scoring elements may possess sufficient elasticity to accommodate such shortening. For example, nitinol and other shape memory alloys possess significant stretchability, typically on the order of 8% which in some instances will be sufficient to accommodate any tension applied on the intermediate scoring section by radial expansion of the balloon.

Referring now to FIGS. 10-12, alternative attachment elements are shown on an embodiment of an expansible scoring cage 140 comprising three helical scoring elements 142 which make up the intermediate scoring section. A first attachment element 146 comprises a single serpentine ring, as best illustrated in FIG. 11 while a second attachment element 148 comprises a pair of tandem serpentine rings 150 and 152, as best illustrated in FIG. 12. The use of such serpentine attachment structures is beneficial since it permits crimping of either or both of the structures onto the catheter body in order to fix either or both ends of the structure thereto. Usually, the single serpentine attachment structure 48 will be affixed to the catheter body while the double serpentine structure will be left free to allow movement of that end of the scoring cage to accommodate radial expansion of the underlying balloon.

Referring now to FIGS. 13 and 14, a further alternative embodiment of an attachment element useful in the scoring cages of the present invention is illustrated. Attachment element 180 includes a pair of serpentine rings 182 and 184, generally as shown in FIG. 12, in combination with a coil spring structure 186 located between said rings 182 and 184. The coil spring structure 186 includes three nested coil springs 190, each joining one of the bend structures 192 and 194 on the serpentine rings 182 and 184, respectively. The structure of the spring structure and adjacent serpentine rings can be understood with reference to the rolled-out configuration shown in FIG. 14.

The attachment structure 180 is advantageous since it permits a fixed attachment of the outermost ring 182 to the underlying catheter body while the inner ring 184 remains floating and expansion and contraction of the intermediate scoring section, comprising helical elements 196, is accommodated by the coil spring structure 186. Since the scoring cage is fixed to the catheter, any risk of loss or slippage from the balloon is reduced while sufficient compliance is provided to easily accommodate radial expansion of the intermediate scoring section. By attaching the structures 180 at at least one, and preferably both ends of the scoring cage, the risk of interference with a stent is reduced.

Figure 15:
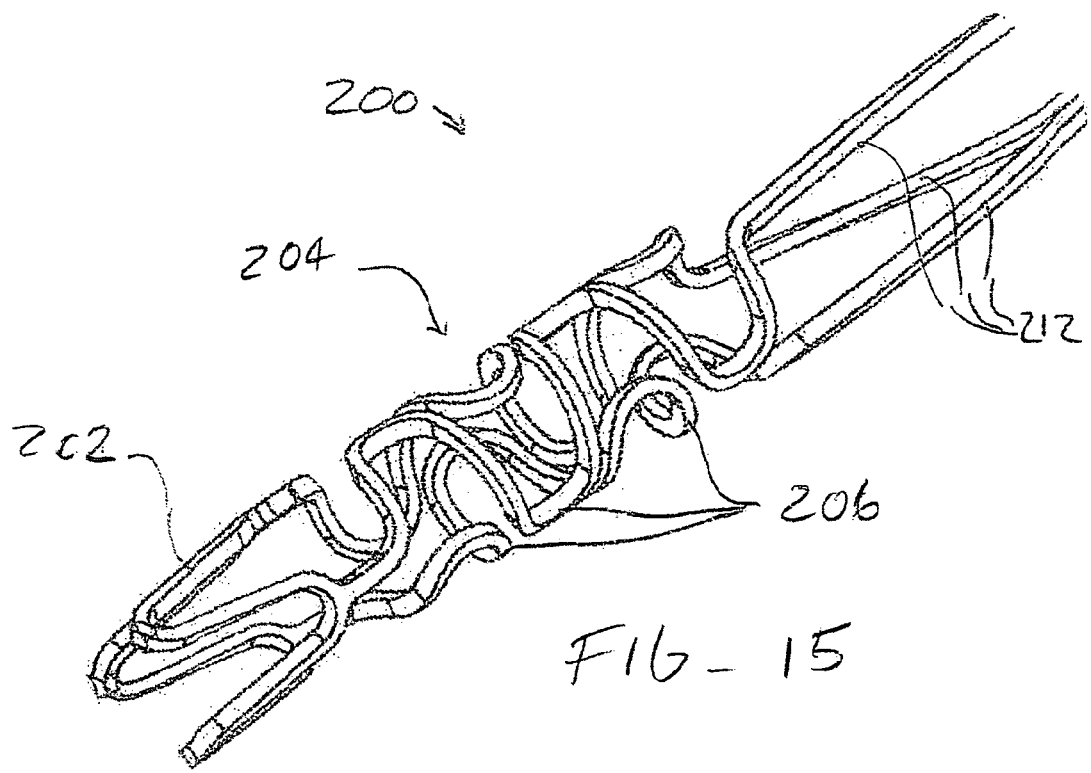
FIG. 15 shows yet another embodiment of a mounting element for the scoring structures of the present invention.
Figure 16:
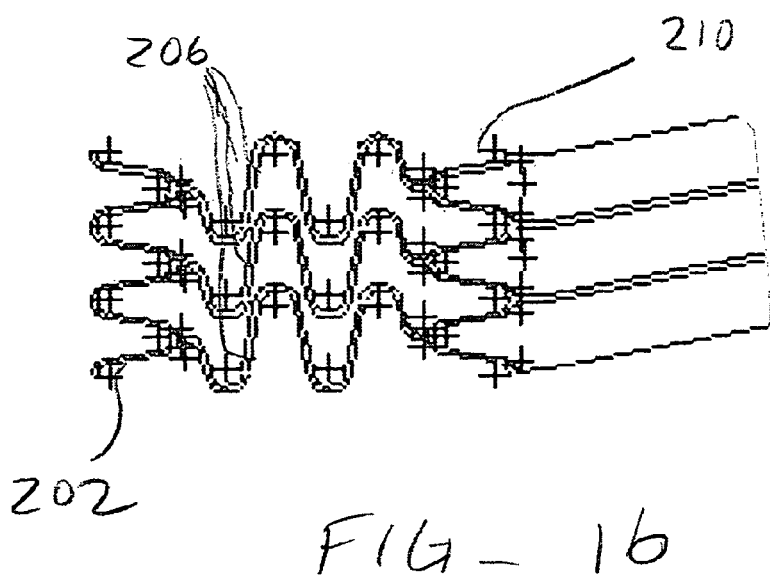
FIG. 16 illustrates the mounting structure of FIG. 15 shown in a rolled-out configuration.

Yet another embodiment of the attachment element of the present invention includes an axial spring as shown in FIGS. 15 and 16. The attachment element 200 includes a terminal serpentine ring 202 and an intermediate spring structure 204 including a number of axial serpentine spring elements 206. The nature of the serpentine ring elements 206 can be observed in the rolled-out configuration of FIG. 16. Optionally, a second serpentine ring 210 may be provided between the attachment structure 200 and the helical scoring elements of the intermediate scoring section 212.

The embodiments of FIGS. 13-16 comprise spring-like elements 186 and 204 to accommodate axial shortening of the scoring structure upon radial expansion. It will be appreciated that other metal and non-metal axially extensible structures could also be used in such attachment structures. For example, elastic polymeric tubes could be attached at one end to the scoring structures and at another end to the catheter body (or to a ring, collar or other structure which in turn is fixed to the catheter body).

As described thus far, the illustrated embodiments have included separate expansible scoring cages which may be placed over an angioplasty or dilatation balloon. As an alternative to the use of such separate scoring cages, scoring elements of the present invention may be attached directly to the expansible balloon or other shell structures, as shown in FIGS. 17-24.

Figure 17:
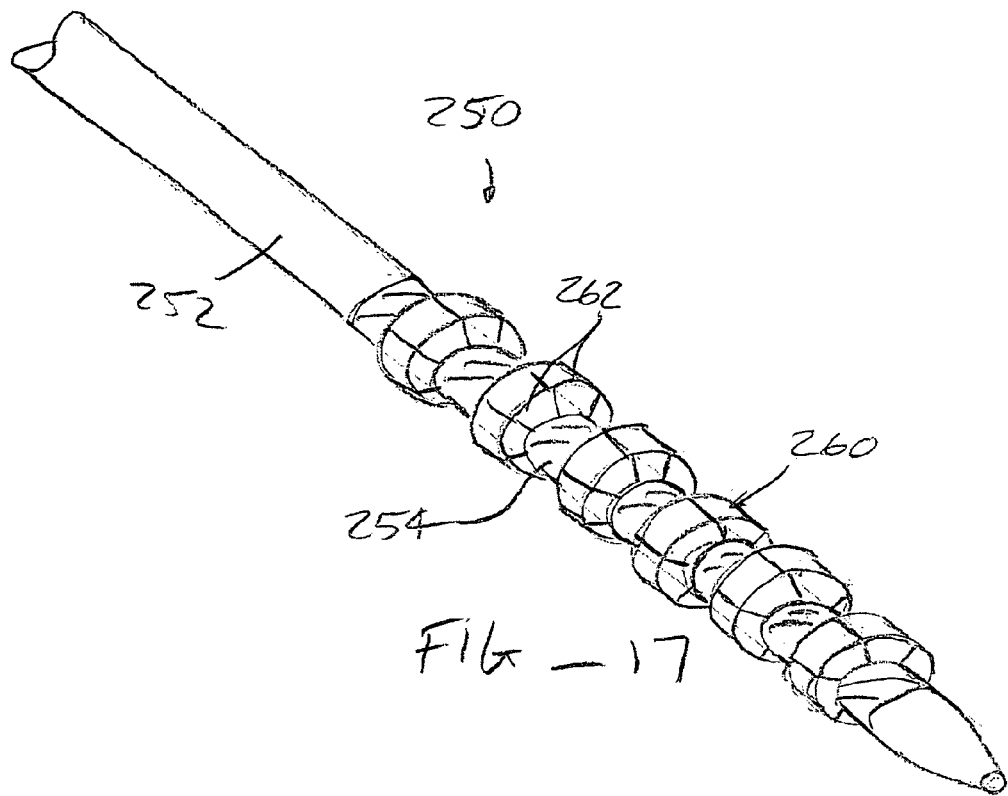
FIG. 17 illustrates yet another alternative embodiment of a catheter constructed in accordance with the principles of the present invention, where the scoring structure comprises a segmented helical element secured directly to the outer surface of the balloon.
Figure 18:
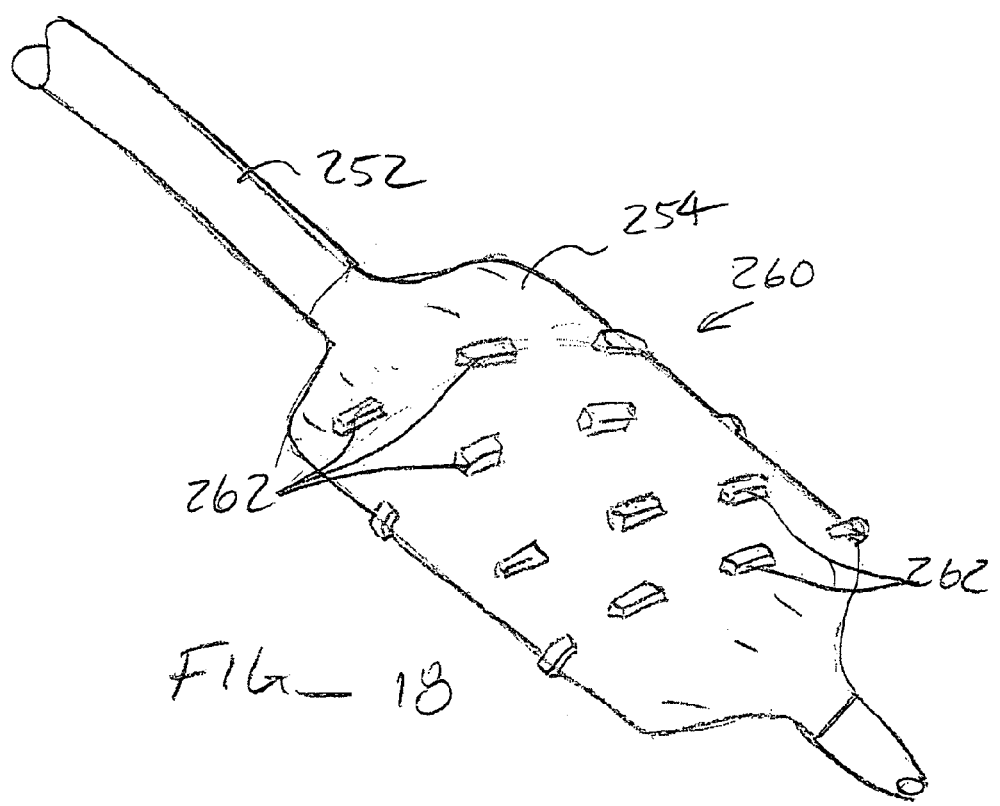
FIG. 18 illustrates the structure of FIG. 17 shown with the balloon inflated.

Referring now to FIGS. 17 and 18, a catheter 250 comprises a catheter body 252 and an expansible balloon 254. A helical scoring structure 260 is formed over and attached directly to an outer surface of the balloon 254 and comprises a plurality of segments 262 which may spread apart as the balloon 254 is inflated, as shown in FIG. 18.

As an alternative to completely independent scoring element segments, scoring elements may comprise expansible rings arranged circumferentially around a balloon, as shown in FIGS. 19-22. In particular, a catheter 280 (FIG. 19) comprising a catheter body 282 and an expansible balloon 284 may have a plurality of elastic, expansible rings 286 disposed at spaced-apart locations along the length of the balloon. The structures 286 will be attached to the balloon, optionally at a single point, so that they remain fixed to the balloon as it expands, as shown in FIG. 20. The expansible rings 286 may comprise expansible diamond elements 290, as best observed in FIG. 20, or may comprise a variety of other conventional expansible ring structures, such as serpentine elements 292 (FIG. 21) or zig-zag structures 294 (FIG. 22). The rings will thus accommodate expansion of the balloon and are elastic so that they will close over the balloon when the balloon is deflated. The use of such separate ring structures may be advantageous in certain circumstances, such as when the balloon is to be expanded in a region of varying diameter so that each ring may accommodate a different diameter.

Referring now to FIGS. 23-24, yet another embodiment of a balloon catheter 300 constructed in accordance with the principles of the present invention will be described. Balloon catheter 300 includes a lobed balloon 302, shown to include three helical lobes, but optionally including a different number of lobes which could be straight or have other configurations. A plurality of scoring elements 310 are arranged over the helical lobes 302, preferably along the helical crowns of the lobes so that they will be engaged against adjacent tissue of the vascular wall when the balloon is inflated.

It will be appreciated by persons skilled in the art that the present invention is not limited to what has been particularly shown and described hereinabove. Alternate embodiments are contemplated that fall within the scope of the invention.

What is claimed is:

1. A scoring catheter comprising:
 a catheter body having a proximal end and a distal end;
 a radially expansible shell near the distal end of the catheter body; and
 a non-axial scoring cage structure carried over the shell so that expansion of the shell expands the cages, wherein said cage structure is unattached to and separate from the shell and includes a plurality of metal helical scoring elements which circumscribe the expansible shell and wherein the helical scoring elements are elastic so that they expand radially as the shell expands and collapse radially as the shell collapses, wherein the helical scoring elements remain over the radially expansible shell as the shell expands and collapses.

2. A catheter as in claim 1, wherein the expansible shell has an expansible area and the scoring cage structure covers a percentage of the expansible area below 20%.

3. A catheter as in claim 2, wherein the percentage is in the range from 1% to 5%.

4. A catheter as in claim 1, wherein the helical scoring elements comprise a wire.

5. A catheter as in claim 1, wherein the scoring cage structure has two ends where one end is attached to the catheter body near one end of the shell and the other end of the scoring cage structure is unattached to the catheter body and is free to slide axially at the other end of the shell.

6. A catheter as in claim 1, wherein at least a portion of the cage is composed of a superelastic material.

7. A catheter as in claim 1, wherein the assembly of the shell and the scoring structure is sufficiently flexible to permit bending at a radius of 10 mm or below when advanced through the coronary vascular.

8. A catheter as in claim 1, wherein the scoring structure comprises a pair of axially spaced-apart attachment structures with at least one scoring element disposed therebetween.

9. A catheter as in claim 8 wherein at least one of the attachment structures is fixed to the catheter body on one side of the radially expansible shell.

10. A catheter as in claim 9, wherein only one of the attachment structures is fixed and the other is adapted to axially slide as the scoring element foreshortens as the shell is expanded.

11. A catheter as in claim 9, wherein both attachment structures are fixed to the catheter structure.

12. A catheter as in claim 11, where in at least one of the attachment structures includes an axially extensible component adapted to accommodate foreshortening of the scoring element as the shell is expanded.

13. A catheter as in claim 8, wherein the scoring element has a scoring edge over at least a portion of its length.

14. A catheter as in claim 13, wherein the scoring element is oriented radially outwardly as the shell is expanded.

15. A catheter as in claim 8, wherein the scoring element is substantially free of a scoring edge.

16. A scoring catheter comprising:
a catheter body having a proximal end and a distal end;
a radially expansible shell disposed near the distal end of the catheter body; and
an elastic scoring cage structure comprising a plurality of metal scoring elements and circumscribing the radially expansible shell, wherein the cage structure has a free end which is not attached to the shell and a fixed end which is attached to the catheter body so that the free end of the cage structure slides axially as the shell expands radially, wherein the cage structure remains over the radially expansible shell as the shell expands and collapses with the radially expansible shell as the shell is expanded and collapsed.

17. A catheter as in claim 16, wherein at least a portion of the scoring cage structure is aligned non-axially over the shell.

18. A catheter as in claim 17, wherein at least a portion of said scoring cage structure is arranged helically over the shell.

19. A catheter as in claim 17, wherein at least a portion of said scoring cage structure is arranged in a serpentine pattern over the shell.

20. A catheter as in claim 17, wherein at least a portion of said scoring cage structure is arranged circumferentially over the shell.

21. A catheter as in claim 16, wherein the expansible shell has an expansible area and the scoring cage structure covers a percentage of the expansible area below 20%.

22. A catheter as in claim 21, wherein the percentage is in the range from 1% to 5%.

23. A catheter as in claim 16, wherein at least a portion of the scoring cage structure comprises a wire.

24. A catheter as in claim 16, wherein the scoring cage structure is arranged to radially close over the expansible shell when the shell is collapsed.

25. A catheter as in claim 16, wherein at least a portion of the scoring cage structure is composed of a superelastic material.

26. A catheter as in claim 16, wherein the assembly of the shell and the scoring cage structure is sufficiently flexible to permit bending at a radius of 10 mm or below when advanced though the coronary vascular.

27. A catheter as in claim 16, wherein the scoring cage structure comprises one or more scoring elements, wherein less than 70% of the cumulative length of the scoring elements is aligned axially on the shell when expanded.

28. A catheter as in claim 27, wherein less than 50% of the cumulative length is aligned axially.

29. A catheter as in claim 28, wherein less than 25% of the length is aligned axially.

30. A catheter as in claim 16, wherein the non-axial scoring structure comprises one or more scoring elements having a scoring edge, wherein the cumulative length of the scoring edge includes a non-axial component of at least 10 mm.

31. A catheter as in claim 30, wherein the non-axial component is at least 12 mm.

32. A catheter as in claim 31, wherein the non-axial component is at least 36 mm.

33. A catheter as in claim 16, wherein the scoring structure comprises a pair of axially spaced-apart attachment structures with at least one scoring element disposed therebetween, wherein only one of the attachment structures is fixed and the other is adapted to axially slide as the scoring element foreshortens as the shell is expanded.

34. A catheter as in claim 33, wherein at least one of the attachment structures is fixed to the catheter body on one side of the radially expansible shell.

35. A catheter as in claim 33, wherein at least one of the attachment structures includes an axially extensible component adapted to accommodate foreshortening of the scoring element as the shell is expanded.

36. A catheter as in claim 33, wherein the scoring element has a scoring edge over at least a portion of its length.

37. A catheter as in clam 36, wherein the scoring element is oriented radially outwardly as the shell is expanded.

38. A catheter as in claim 33 wherein the scoring element is substantially free of a scoring edge.

39. An expansible scoring cage adapted to be carried over a balloon of a balloon catheter, said cage comprising:
an assembly of one or more elongate helical elastic scoring elements, wherein said assembly is normally in a radially collapsed configuration and expansible over a balloon to a radially expanded configuration, wherein the assembly returns to its radially collapsed configuration when the balloon is deflated;
wherein the scoring elements are metal and adapted to score hardened stenotic material when expanded by the balloon in a blood vessel lumen wherein said one or more elongate helical scoring elements are disposed between a pair of collars, wherein said collars are adapted to be mounted over the catheter with the balloon therebetween and the collars hold the scoring elements over the balloon as the balloon is inflated and deflated.

40. A scoring cage as in claim 39, wherein one of said collars is fixable to the catheter body and the other is free to slide axially over the catheter body.

41. A scoring cage as in claims 39 and 40, wherein at least a portion of the scoring element assembly is adapted to circumscribe the balloon.

42. A scoring cage as in claim 39, wherein the balloon has an expanded area and the scoring elements covers a percentage of the expanded area below 10%.

43. A scoring cage as in claim 42, wherein the percentage is in the range from 1% to 5%.

44. A catheter as in claim 39, wherein at least a portion of the scoring structure comprises a wire.

45. A scoring cage as in claim 39, wherein the scoring elements are elastic and arranged to radially close over the balloon when the balloon is deflated.

46. A scoring cage as in claim 39, wherein at least a portion of the scoring element assembly is composed of a superelastic material.

47. An expansible scoring case as in claim 39, wherein the scoring cage is sufficiently flexible to permit bending at a radius of 10 mm or below when advanced through the coronary vasculature.

48. A cage as in claim 39, wherein the elastic scoring elements have scoring edges.

49. A method for dilatating a stenosed region in a blood vessel, said method comprising:

expanding an expansible shell to radially expand an elastic scoring structure within a stenosed region within the blood vessel, wherein said scoring structure is unattached to and separate from the shell and includes one or more elastic metal helical scoring segments, wherein the elastic scoring elements are disposed between the shell and the stenosed region and expanding the shell causes the elastic scoring elements to penetrate into stenotic material to impart a helical score pattern in the stenotic material about the inner wall of the blood vessel as the shell is expanded; and radially contracting the shell, wherein the scoring structure remains over the shell as the shell is expanded and contracted.

50. A method as in claim 49, wherein the stenosed region is characterized by the presence of calcified plaque, wherein the plaque is scored as the region is dilated.

51. A method as in claim 49, wherein the scoring structure is not substantially moved in an axial direction while engaged against the stenosed region.

52. A method as in claim 49, wherein the scoring structure covers less than 5% of the wall area of the stenosed region.

53. A method as in claim 49, wherein the scoring structure is at least partly elastic and exerts a radially compressive force to help close the expansible shell as the shell is deflated.

54. A method as in claim 49, further comprising advancing an assembly of the radially expandable shell and the scoring structure through the coronary vasculature, wherein the assembly is adapted to permit bending at a radius of 10 mm or below as the assembly is advanced.

* * * * *